United States Patent [19]

Walsh et al.

[11] Patent Number: 5,086,055

[45] Date of Patent: Feb. 4, 1992

[54] SERIES OF 5-[-(4-ARYL-1-PIPERAZINYL)ALKYL]-2-OXAZOLIDINONE DERIVATIVES USEFUL IN THE TREATMENT OF ALLERGIC CONDITIONS

[75] Inventors: David A. Walsh, Richmond, Va.; John M. Yanni, Fort Worth, Tex.

[73] Assignee: A. H. Robins Company, Incorporated, Richmond, Va.

[21] Appl. No.: 633,030

[22] Filed: Dec. 24, 1990

[51] Int. Cl.$^5$ .............................. A61K 31/50
[52] U.S. Cl. ..................... 514/252; 514/826
[58] Field of Search ................ 514/252, 826

[56] References Cited

U.S. PATENT DOCUMENTS

| | | | |
|---|---|---|---|
| 3,419,559 | 12/1968 | Lunsford et al. | 260/268 |
| 3,423,418 | 1/1969 | Lunsford et al. | 260/307 |
| 3,455,941 | 7/1969 | Lunsford et al. | 260/295 |
| 3,457,267 | 7/1969 | Lunsford et al. | 260/294 |
| 3,513,236 | 5/1970 | Lunsford et al. | 424/267 |
| 4,886,794 | 12/1989 | Walsh | 514/326 X |

Primary Examiner—Leonard Schenkman

[57] ABSTRACT

A method of treating allergic disorders and pharmaceutical compositions therefore are disclosed for a series of 5-[(4-aryl-1-piperazinyl)alkyl]-2-oxazolidinone derivatives of Formula I. These compounds are useful in inhibiting Type I allergic

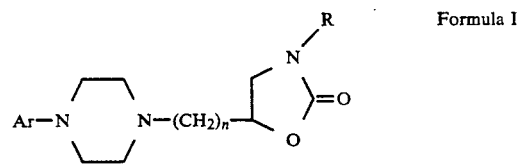

Formula I responses in a living animal and thus can be used to treat allergic phenomena such as asthma, rhinitis, atopic dermatitis, chronic hives, allergic conjunctivitis and the like.

12 Claims, No Drawings

SERIES OF 5-[-(4-ARYL-1-PIPERAZINYL)ALKYL]-2-OXAZOLIDINONE DERIVATIVES USEFUL IN THE TREATMENT OF ALLERGIC CONDITIONS

BACKGROUND OF THE INVENTION

1. Field of Invention

This invention relates to 5-[(4-aryl-1-piperazinyl)alkyl]-2-oxazolidinone derivatives, some of which have not been specifically disclosed before, that are useful in a method of treating allergic conditions and in a pharmaceutical composition for treating allergic conditions in warm blooded animals.

2. Information Disclosure Statement

U.S. Pat. Nos. 3,419,559; 3,455,941; 3,513,236 and 3,457,267 disclose compounds of this invention having the generic formula

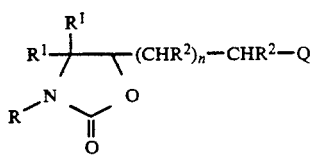

Formula A where
$R = H$, loweralkyl, cycloalkyl, benzyl;
$R^1 = H$, loweralkyl independently;
$R^2 = H$, loweralkyl;
$n = 1$ or 2; and
where Q includes

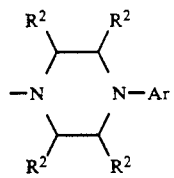

and Ar is phenyl, phenyl substituted by 1-3 substituents selected from loweralkyl, loweralkoxy, nitro, thioloweralkyl diloweralkylamino, trifluoromethyl, halogen, hydroxy and the like; 2-quinolinyl, or 2-pyridinyl.

These compounds were disclosed as having tranquilizing and analgesic properties.

A related patent, U.S. Pat. No. 3,423,418 disclosed 2-oxazolidinones having the formula

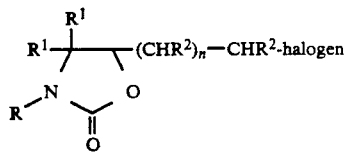

Formula B which are intermediates useful in the preparation of the Formula A compounds.

U.S. Pat. No. 4,886,794 discloses antiallergy 4-[(α,α-diaryl)hydroxymethyl]-1-piperidinylalkyl-cyclic carbamates of Formula C which encompasses the 5-substituted 2-oxazolidinones.

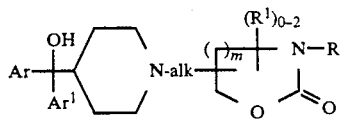

Formula C

SUMMARY OF THE INVENTION

A method of treating allergies, more specifically the Type I allergic response (Gell and Coombs classification), has been discovered in a series of compounds of

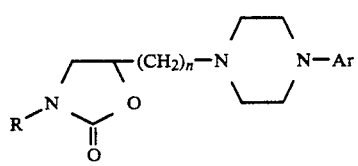

Formula I

Formula I which are disclosed by our aforementioned U.S. Patents as shown by Formula A hereinabove

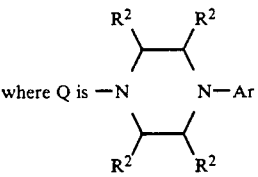

where Q is

Under Formula I, R is hydrogen, loweralkyl, phenyl, substituted phenyl, phenylloweralkyl or cycloalkyl; n is 1-4, and Ar is pyridinyl, phenyl, or phenyl substituted by from 1 to 3 substituents selected from halogen, loweralkyl, loweralkoxy, trifluoromethyl, nitro, acetyl, amino, loweralkylamino, diloweralkylamino, acetylamino, cyano, aminocarbonyl, or carboxylate; the stereoisomers, and the pharmaceutically acceptable salts thereof.

Terms used in the above description of Formula I and elsewhere in the specification and claims are further defined as follows:

Loweralkyl, unless further specified, includes straight and branched chain hydrocarbons of from 1-6 carbons inclusive and is exemplified by groups such as methyl, ethyl, propyl, isopropyl, butyl, t-butyl, isobutyl, pentyl, isopentyl and hexyl. Loweralkoxy is defined as —O-loweralkyl. Phenylloweralkyl includes such groups as benzyl, benzhydryl, or phenethyl. The terms loweralkylamino and diloweralkylamino refer to such groups as methylamino, dimethylamino, ethylamino, diethylamino, propylamino, isopropylamino, t-butylamino, dipropylamino and the like. Cycloalkyl refers to a cyclic hydrocarbon having from 3 to 5 carbons, such as cyclopropyl, cyclopentyl, or cyclohexyl. Halogen includes fluorine, chlorine, bromine or iodine. The term carboxylate means a carboxylic acid as a derivative thereof such as an ester or amide. Stereoisomers mean the optical isomers or diastereomers, where they exist. The term pharmaceutically acceptable salt includes solvates, hydrates, and non-toxic acid addition salts formed from mineral acids such as hydrochloric acid, hydrobromic acid, sulfuric acid or phosphoric acid and salts formed from organic acids such as fumaric acid, maleic acid, oxalic acid, tartaric acid, hexamic acid, and the like.

The primary screening method used to detect antiallergy properties of the compounds of Formula I is a modification of the procedure of R. R. Martel and J. Klicius, Intern. Arch. Allergy Appl. Immunology, Vol. 54, pp 205–209 (1977) which measures the effect of oral administration of the compound on the volume of a rat paw which was previously injected with anti-egg albumin serum and is described in detail under Pharmacology Methods hereinbelow.

The above test is useful in determining the ability of a compound to inhibit Type I allergic responses in a living animal and their usefulness in treating allergic phenomena which includes asthma, rhinitis, atopic dermatitis, chronic hives, allergic conjunctivitis and the like.

The Gell and Coombs Classification of Immune Responses referred to hereinabove is well known in the art and is described in Essential Immunology, 3rd Ed. (1977) (Blackwell Scientific Publications) printed by William Clowes & Sons, Limited London, Beccles and Colchester.

It is an object of this invention to provide a method of treating allergic disorders including the Type I allergic response. Another object is to provide a pharmaceutical composition providing a suitable dosage form for the compounds of this invention.

DETAILED DESCRIPTION OF INVENTION

Many of the compounds used in this invention, the intermediates, and methods for preparation of the intermediates and invention compounds have been disclosed in our U.S. Pat. Nos. 3,419,559; 3,455,941; 3,513,236; 3,457,267 and 3,423,418. Some other intermediates are disclosed in our U.S. Pat. No. 4,886,794. These patents are herein incorporated by reference.

The compounds used in the methods of this invention are prepared by the following general scheme.

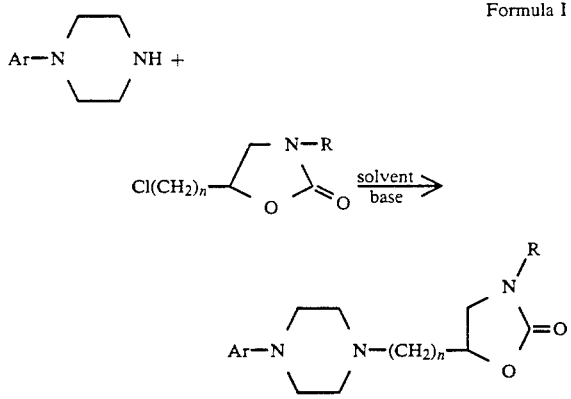

The 1-arylpiperizines are all known compounds and are commercially available or can be prepared by the methods described in Jain et. al., J. Med. Chem., 10, 812–818 (1967). The 3-substituted-5-(haloalkyl)-2-oxazolidinones have been described previously in the incorporated patents and in Fielden et. al., J. Med. Chem., 16, 1124–1128 (1973); Li and Biel, J. Org. Chem., 35, 4100–4103 (1970); and Darling and Beauchamp, J. Pharm. Sci., 58, 362–364 (1969).

The preparations of compounds used in the methods of this invention which have not been specifically disclosed previously and the intermediates thereto are given in the following preparations and examples.

Stereoisomers are separated using standard techniques for resolution of optically active compounds or are prepared from optically active starting materials.

PREPARATION 1

1-(3,4,5-Trimethoxyphenyl)piperazine

A solution of 44.3 g (0.25 mol) of bis(2-chloroethyl)amine hydrochloride and 45.5 g (0.25 mol) of 3,4,5-trimethoxyaniline in 550 mL of absolute ethanol was heated at reflux for 16 h under a nitrogen atmosphere. The mixture was cooled and 50.0 g (0.36 mol) of potassium carbonate was added and heating was continued for 16 h. The hot mixture was filtered, the filtrate was concentrated under reduced pressure and the residue was triturated with ethyl acetate. The collected solid was recrystallized from 2-propanol/methanol. The solid was dissolved in 5.9N sodium hydroxide and the solution was continuously extracted with chloroform for 5 h. The organic layer was dried (MgSO$_4$), concentrated under reduced pressure, and the residue was triturated with cyclohexane/petroleum ether (30°–60°) to give 23.6 g (38%) of white solid, mp 73°–77° C.

Anal. Calculated for $C_{13}H_{20}N_2O_3$: C, 61.89; H, 7.99; N, 11.10. Found: C, 61.53; H, 8.01; N, 11.01.

PREPARATION 2

1-(3,4-Dichlorophenyl)piperazine

This compound was prepared according to the procedure used in Preparation 1. A mixture of 44.6 g (0.25 mol) of bis(2-chloroethyl)amine hydrochloride, 40.5 g (0.25 mol) of 3,4-dichloroaniline and 50.0 g (0.362 mol) of potassium carbonate in a total volume of 500 mL of n-butanol gave an oil as residue. Trituration of the oil with petroleum ether (30°–60°) gave 16.0 g (28%) of white solid, mp 62°–65° C.

Anal. Calculated for $C_{12}H_{18}N_2Cl_2$: C, 51.97; H, 5.23; N, 12.12. Found: C, 51.75; H, 5.24; N, 12.01.

PREPARATION 3

1-(3,4-Dimethoxyphenyl)piperazine

This compound was prepared according to the procedure of Preparation 1. A mixture of 53.3 g (0.3 mol) of bis(2-chloroethyl)amine hydrochloride, 45.7 g (0.03 mol) of 4-aminoveratrole and 124.0 g (0.9 mol) of solid potassium carbonate in a total volume of 500 mL of absolute ethanol gave a purple solid after trituration with ethyl acetate. The collected solid was recrystallized from aqueous methanol to give 19.8 g of white hydrochloride salt. The salt was converted to the base which solidified. Trituration of the solid with petroleum ether (30°–60° C.) gave 12.0 g (18%) of pinkish-white solid, mp 62°–65° C.

Anal. Calculated for $C_{12}H_{18}N_2O_2$: C, 64.84; H, 8.16; N, 12.60. Found: C, 64.50; H, 8.15; N, 12.48.

PREPARATION 4

1-(4-Methylphenyl)piperazine Dihydrochloride

This compound was prepared according to the procedure used in Preparation 1. A mixture of 53.5 g (0.3 mol) of bis(2-chloroethyl)amine hydrochloride, 32.1 g (0.3 mol) of p-toluidine and 50.0 g (0.4 mol) of solid potassium carbonate in a total volume of 400 mL of n-butanol gave an oil that crystallized upon trituration with ethyl acetate. The hydrochloride was converted to the base which solidified. The solid was triturated with a petroleum ether (30°–60° C.)/ethyl ether mixture to give 21.0 g (40%) of collected solid. A 1.6 g portion of the base was converted to the hydrochloric acid salt and recrystallized from methanol/ethyl ether to give 1.7 g of white solid, mp 215° C. (dec).

Anal. Calculated for $C_{11}H_{18}Cl_2N_2$: C, 53.02; H, 7.28; N, 11.24. Found: C, 53.30; H, 7.41; N, 11.45.

PREPARATION 5

1-(4-Bromophenyl)Piperazine Monohydrochloride

This compound was prepared according to the procedure of Preparation 1. A mixture of 5.4 g (0.03 mol) of bis(2-chloroethyl)amine hydrochloride, 5.2 g (0.03 mol) of p-bromoaniline and 5.0 g (0.04 mol) of solid potassium carbonate in a total volume of 50 mL of absolute ethanol gave 2.9 g (26%) of a semisolid. A 0.5 g portion of the base was converted to the hydrochloric acid solid and recrystallized from methanol/ethyl ether to give a white solid, mp 240° C. (dec.)

Anal. Calculated for $C_{10}H_{14}BrClN_2$: C, 43.27; H, 5.11; N, 10.12. Found: C, 43.01; H, 5.08; N, 10.09.

PREPARATION 6

1-(4-Nitrophenyl)Piperazine

This compound was prepared according to the procedure of Preparation 1. A mixture of 100.0 g (0.56 mol) of bis(2-chloroethyl)amine hydrochloride, 77.3 g (0.56 mol) of p-nitroaniline and 160.0 g (1.2 mol) of solid potassium carbonate in a total volume of 1 L of n-butanol gave an oil that solidified upon trituration with ethyl acetate. The hydrochloric acid salt was converted to the base which solidified. The solid was triturated with ethyl ether/methanol to give 16.1 g (14%) of the product. Concentration of the ethyl ether/methanol mixture gave 1.3 g as a light yellow solid, mp 121°-123° C.

Anal. Calculated for $C_{10}H_{13}N_3O_2$: C, 57.96; H, 6.32; N, 20.28. Found: C, 57.84; H, 6.29; N, 20.37.

PREPARATION 7

1-(2,4-Dimethoxyphenyl)Piperazine Dihydrochloride

This compound was prepared according to the procedure of Preparation 1. A mixture of 53.6 g (0.3 mol) of bis(2-chloroethyl)amine hydrochloride, 45.6 g (0.3 mol) of 2,4-dimethoxyaniline and 83.0 g (0.6 mol) of solid potassium carbonate in a total volume of 500 mL of absolute ethanol gave a purple solid when concentrated under reduced pressure and triturated with ethyl acetate. The solid was recrystallized twice from methanol-ethyl ether to give 31.0 g of light purple compound. The salt was converted to the base using 10% sodium hydroxide to give 22.8 g (34%) of brown oil. An 1.5 g portion of this oil was converted to the hydrochloride in ethereal HCl. The collected solid was recrystallized from methanol-ethyl ether to give 1.1 g of white solid, mp 230°-233° C.

Anal. Calculated for $C_{12}H_{20}Cl_2N_2O_2$: C, 48.82; H, 6.83; N, 9.49. Found: C, 49.19; H, 6.97; N, 9.67.

PREPARATION 8

1-(3-Fluorophenyl)Piperazine Monohydrochloride

This compound was prepared according to the procedure of Preparation 1. A mixture of 8.0 g (0.045 mol) of bis(2-chloroethyl)amine hydrochloride, 5.0 g (0.045 mol) of m-fluoroaniline and 12.5 g (0.09 mol) of solid potassium carbonate in a total volume of 50 mL of n-butanol gave 3.5 g (35%) of white solid, mp 205°-207° C. (methanol-water-ethyl ether).

Anal. Calculated for $C_{10}H_{14}ClFN_2$: C, 55.43; H, 6.51; N, 12.93. Found: C, 55.30; H, 6.59; N, 13.10.

PREPARATION 9

4-(1-Piperazinyl)Benzonitrile Monohydrochloride

A mixture of 27.3 g (0.15 mol) of p-bromobenzonitrile, 38.7 g (0.45 mol) of piperazine and 42.0 g (0.30 mol) of solid potassium carbonate in a total volume of 60 mL of n-butanol was heated at reflux for 6 h under a nitrogen atmosphere. The mixture was concentrated under reduced pressure and the slurry partitioned between 10% sodium hydroxide and chloroform. The chloroform layer was separated, dried (MgSO$_4$) and concentrated under reduced pressure to give an oil. The oil was eluted through a 400 g silica gel column with a 10% methanol in methylene chloride mixture. The appropriate fractions were concentrated under reduced pressure to give a golden oil. Trituration of this oil with ethyl acetate gave a white powder. The collected white powder was stirred for 15 min in ethereal HCl and recrystallized from methanol-water to give 1.5 g (4.5%)* of white solid, mp>160° C. with decomposition.

* The yield was increased to 20% when anhydrous piperazine was used.

Anal. Calculated for $C_{11}H_{14}ClN_3$: C, 59.06; H, 6.31; N, 18.78. Found: C, 58.90; H, 6.32; N, 18.66.

PREPARATION 10

1-(2-Fluorophenyl)piperazine monohydrochloride

This compound was prepared according to the procedure used in Preparation 1. A mixture of 15.1 g (0.09 mol) of bis(2-chloroethyl)amine hydrochloride, 10.0 g (0.09 mol) of 2-fluoroaniline and 25.0 g of solid potassium carbonate in a total volume of 100 mL of 1-butanol gave an oil as residue. The oil was converted to the hydrochloric acid salt (ethereal HCl) and recrystallized from methanol-ether to give 4.0 g (20%) of white solid, mp 185°-187° C.

Anal. Calculated for $C_{10}H_{14}ClFN_2$: C, 55.43; H, 6.51; N, 12.93. Found: C, 55.24; H, 6.57; N, 12.96.

PREPARATION 11

4-(1-Piperazinyl)benzamide

To 8.0 g (0.04 mol) of 4-(1-piperazinyl)benzonitrile was added, with stirring, 50.0 mL (0.87 mol) of 93% sulfuric acid over a 15 min period. The mixture was stirred overnight and the resulting suspended amide was collected by filtration, rinsed with water, and allowed to air dry. The solid was recrystallized from absolute ethanol to give 1.6 g (20%) of white solid, mp 240°-243° C.

Anal. Calculated for $C_{11}H_{15}N_3O$: C, 64.37; H, 7.37; N, 20.47. Found: C, 64.20; H, 7.33; N, 20.34.

PREPARATION 12

1-(4-Nitrophenyl)-4-(phenylmethyl)piperazine

To 12.5 g (0.07 mol) of mechanically stirred 1-benzylpiperazine was added 10.0 g (0.07 mol) of 4-nitrofluorobenzene. After 10 minutes of a mildly exothermic reaction, the mixture solidified. The yellow solid was suspended in 50 mL of ethyl acetate and ethereal HCl was slowly added to the stirring mixture under a nitrogen atmosphere. The solid was collected (filtration) and partitioned between 10% sodium hydroxide solution and benzene. The benzene layer was washed with ten 100 mL portions of water, dried with anhydrous magnesium sulfate and concentrated under reduced pressure to give a yellow oil. Upon cooling, the oil crystallized. The solid was recrystallized from 2-propanol/petroleum ether (60°–110°) to give 9.8 g (47%) of yellow solid, mp 115°–118° C.

Anal. Calculated for $C_{17}H_{19}N_3O_2$: C, 68.67; H, 6.44; N, 14.13. Found: C, 68.87; H, 6.43; N, 14.18.

PREPARATION 13

4-[4-(Phenylmethyl)-1-piperazinyl]benzamine dihydrochloride

This compound was prepared by the hydrogenation of 9.8 g (0.03 mol) of 1-(4-nitrophenyl)-4-(phenylmethyl)piperazine in 200 mL of benzene using palladium on carbon as the catalyst. The solution was filtered and the filtrate concentrated to an oil under reduced pressure. Upon cooling, the oil crystallized to a dark purple mass. The solid was triturated with petroleum ether (60°–110°) for 1 h and 9.5 g (50%) of light purple product was collected by filtration. One gram of this unstable solid was converted to the hydrochloride salt (ethereal HCl) and recrystallized from methanol/ethyl ether to give 100 mg of light purple solid, mp>240° C.

Anal. Calculated for $C_{17}H_{23}Cl_2N_3$: C, 60.00; H, 6.81; N, 12.35. Found: C, 60.09; H, 6.83; N, 12.33.

PREPARATION 14

N-[4-[4-(Phenylmethyl)-1-piperazinyl]phenyl]acetamide

To a solution of 8.5 g (0.03 mol) of 4-[4-(phenylmethyl)-1-piperazinyl]benzeneamine and 16.0 g (0.16 mol) of triethylamine in 450 mL of ethyl acetate was added, dropwise, a solution of 2.5 g (0.035 mol) of acetyl chloride in 50 mL of ethyl acetate. The mixture was magnetically stirred for 3 h and then heated at reflux for 1 h. The excess acetyl chloride was co-distilled with benzene and the resulting oil was shaken in 400 mL of 10% sodium hydroxide solution. The suspended tan solid was collected by filtration, washed thrice with 100 mL portions of water, and air dried to give 9.7 g (99%) of crude product. A one-gram portion was recrystallized from benzene/petroleum ether to give 100 mg of cream colored solid, mp 159°–161° C.

Anal. Calculated for $C_{19}H_{23}N_3O$: C, 73.76; H, 7.49; N, 13.58. Found: C, 73.65; H, 7.44; N, 13.48.

PREPARATION 15

N-[4-(1-Piperazinyl)Phenyl]Acetamide

This compound was prepared by the hydrogenation of 7.7 g (0.025 mol) of N-[4-[4-(phenylmethyl)-1-piperazinyl]phenyl]acetamide in 100 mL of methanol using palladium on carbon as the catalyst. The solution was filtered and the filtrate concentrated under reduced pressure to give an oil which crystallized. The solid was dissolved in a minimum amount of a methylene chloride/10% methanol solution and passed through a 100 g Florisil column. The desired fractions were concentrated to an oil under reduced pressure which crystallized to give 3.1 g (56%) of crude product. A 0.5 g portion was recrystallized from methanol/petroleum ether to give a cream colored solid, mp 191°–193° C.

Anal. Calculated for $C_{12}H_{17}N_3O$: C, 65.73; H, 7.81; N, 19.16. Found: C, 65.64; H, 7.75; N, 19.10.

PREPARATION 16

4-(1-Piperazinyl)Benzoic Acid Ethyl Ester Monohydrochloride

To 3.1 g (0.015 mol) of 4-(1-piperazinyl)benzamide suspended in 5.0 mL (0.09 mol) of 95% ethyl alcohol was added, dropwise, 3.0 mL (0.06 mol) of 90% sulfuric acid under ice bath temperature. The mixture was heated at reflux for 5 h and then neutralized with 10% sodium hydroxide under ice bath temperature. The suspended solid (starting material) was collected by filtration and the filtrate was extracted thrice with 25 mL portions of benzene. The combined benzene extracts were dried (magnesium sulfate) and concentrated under reduced pressure to give a golden oil. The hydrochloride was formed in 2-propanol saturated with HCl and the collected solid (1.1 g, 31%) was recrystallized from 2-propanol to give 0.5 g of white crystalline solid, mp 203°–206° C.

Anal. Calculated for $C_{13}H_{19}ClN_2O_2$: C, 57.67; H, 7.07; N, 10.35. Found: C, 57.52; H, 7.13; N, 10.38.

PREPARATION 17

4-Fluoro-3-Methylbenzenamine Monohydrochloride

A solution of 20.0 g (0.129 mol) of 2-fluoro-5-nitrotoluene in 150 mL of tetrahydrofuran was added to a large Parr bottle along with ½ teaspoon of 5% Pd/C catalyst. The reaction mixture was hydrogenated at room temperature until 3 equivalents of hydrogen had been taken up (approx. 30 min). The solution was filtered through Celite and the filtrate concentrated under reduced pressure to yield 18.0 g (100%) of a yellow oil. A portion of the oil was converted to the hydrochloric acid salt and the solid was recrystallized from 2-propanol to yield an off-white solid, mp 257°–260° C., which contained a small amount of water.

Anal. Calculated for $C_7H_9ClFN \cdot 0.25\ H_2O$: C, 50.62; H, 5.77; N, 8.43. Found: C, 50.89; H, 5.68; N, 8.65.

PREPARATION 18

1-(3-Ethylphenyl)Piperazine Monohydrochloride

A solution of 73.3 g (0.411 mol) of bis(2-chloroethyl)amine hydrochloride and 49.7 g (0.411 mol) of 3-ethylaniline in 500 mL of absolute ethanol was heated at reflux for 16 h under a nitrogen atmosphere. The mixture was cooled and 85.2 g (0.617 mol) of anhydrous potassium carbonate was added and heating was continued for 16 h. The hot mixture was filtered and the filtrate was concentrated under reduced pressure. The residue was triturated with ethyl acetate to yield 65.7 g (71%) of solid. A portion of this crude product was recrystallized from 2-propanol to yield a white crystalline solid, mp 194°–195° C.

Anal. Calculated for $C_{12}H_{19}ClN_2$: C, 63.57; H, 8.45; N, 12.35. Found: C, 63.46; H, 8.58; N, 12.32.

PREPARATION 19

1-(4-Fluoro-3-Methylphenyl)Piperazine Dihydrochloride

A solution of 56.3 g (0.315 mol) of bis(2-chloroethyl)amine hydrochloride and 35.9 g (0.287 mol) of 4-fluoro-3-methylbenzeneamine in 500 mL of absolute ethanol was heated at reflux for 24 h under a nitrogen atmosphere. The mixture was cooled and 65.3 g (0.473 mol) of anhydrous potassium carbonate was added and heating was continued for 24 h. The hot mixture was filtered and the filtrate was concentrated under reduced pressure. The residue was triturated with ethyl acetate to yield a crude solid. This solid was converted to the base and purified by column chromatography using 500 g of silica gel on a 30 cm×10 cm column, eluted with methanol. The fractions containing the product were combined and concentrated. The residue was partitioned between water and ethyl ether. The ethyl ether layer was washed with water, dried (MgSO$_4$) and concentrated under reduced pressure to yield 9.3 g (14%) of a light-pink oil. A portion of the oil was converted to the dihydrochloric acid salt and the solid was recrystallized from 2-propanol to yield a white solid, mp 188°–191° C.

Anal. Calculated for $C_{11}H_{17}Cl_2FN_2$: C, 49.45; H, 6.42; N, 10.49. Found: C, 49.31; H, 6.51; N, 10.44.

PREPARATION 20

5-(Chloromethyl)-3-Methyl-2-Oxazolidinone

A solution of 64.5 g (0.5 mol) of 1,3-dichloro-2-propanol (Eastman, practical) in 200 mL of methylene chloride was treated with 28.5 g (0.5 mol) of methyl isocyanate and a few drops of triethylamine and allowed to stir at ambient temperature overnight. The solution was concentrated and the residue was dissolved in 200 mL of 95% ethanol and treated with a solution of 33.6 g (0.6 mol) of potassium hydroxide in 300 mL of 95% ethanol. The mixture was stirred at ambient temperature for 3.5 h and then concentrated. The residue was partitioned between 250 mL of benzene and 100 mL of water. The organic layer was washed successively with 50 mL of a 2N hydrochloric acid solution and 100 mL brine, dried (Na$_2$SO$_4$) and concentrated to give 50.5 g of oil which was subjected to vacuum distillation to yield 36.9 g (49%) of clear oil, bp 131°–133° C. (0.3 mm).

Anal. Calculated for $C_5H_8ClNO_2$: C, 40.15; H, 5.39; N, 9.36. Found: C, 38.77; H, 5.39; N, 9.08.

PREPARATION 21

S-(−)-5-(2-Chloroethyl)-3-Methyl-2-oxazolidinone

A solution of 102.9 g (1.04 mol) of phosgene in 500 mL of methylene chloride was added dropwise a solution of 105.3 g (1.04 mol) of S-(+)-1-methyl-3-pyrrolidinol in 250 mL of methylene chloride at such a rate that the internal temperature did not exceed 15° C. After the addition was complete, the solution was stirred at ice bath temperatures for 0.75 h and then treated dropwise with 145 mL (105 g, 1.04 mol) of triethylamine at such a rate that the temperature did not exceed 25° C. The mixture was stirred at ambient temperature for 3 h and then treated with a solution of 50 mL of concentrated hydrochloric acid in 500 mL of water. The layers were separated and the organic layer was washed once with 500 mL of a 4% sodium hydroxide solution, dried (Na$_2$SO$_4$) and concentrated under reduced pressure to give an oil as residue. The oil was subjected to vacuum distillation and 99.3 g (61%) of clear oil, bp 128° C. @ 0.5 mm was collected ($[\alpha]_D^{25} = -58.3°$, methanol).

Anal. Calculated for $C_6H_{10}ClNO_2$: C, 44.04; H, 6.16; N, 8.56. Found: C, 43.51; H, 6.24; N, 8.44.

PREPARATION 22

R-(+)-5-(2-Chloroethyl)-3-Methyl-2-Oxazolidinone

To a solution of 133.8 g (1.35 mol) of phosgene in 650 mL of methylene chloride was added dropwise a solution of 136.8 g (1.35 mol) of R-(−)-t-methyl-3-pyrrolidinol in 300 mL of methylene chloride at such a rate that the internal temperature did not exceed 15° C. After the addition was complete, the solution was stirred at ice bath temperatures for 0.75 h and then treated dropwise with 188 mL (136.5 g, 1.35 mol) of triethylamine at such a rate that the temperature did not exceed 25° C. The mixture was stirred at ambient temperature overnight and then treated with a solution of 50 mL of concentrated hydrochloric acid in 500 mL of water. The layers were separated and the organic layer was washed once with 500 mL of a 4% sodium hydroxide solution, dried (Na$_2$SO$_4$) concentrated under reduced pressure to give an oil as residue. The oil was subjected to vacuum distillation and 136.6 g (83%) of clear oil, by 123°–126° C.@ 0.5 mm, was collected ($[\alpha]_D^{25} = +71.1°$, methanol).

Anal. Calculated for $C_6H_{10}ClNO_2$: C, 44.04; H, 6.16; N, 8.56. Found: C, 43.19; H, 6.21; N, 8.38.

PREPARATION 23

5-(2-Chloroethyl)-3-(1-Methylethyl)-2-Oxazolidinone

To a cold (ice bath) solution of 98.5 g (1.0 mol) of phosgene in 500 mL of methylene chloride was added dropwise a solution of 129.2 g (1.0 mol) of 1-isopropyl-3-pyrrolidinol in 250 mL of methylene chloride at such a rate that the temperature did not exceed 10° C. After addition was complete, the mixture was stirred in the cold bath for 1 h and then treated dropwise with 140 mL (101 g, 1.0 mol) of triethylamine at such a rate that the temperature did not exceed 25° C. The mixture was stirred at ambient temperature for 3 h and then treated with 500 mL of a 1N hydrochloric acid solution. The layers were separated and the organic layer was washed successively with 500 mL of a 1N hydrochloric acid solution, 500 mL of a 4% sodium hydroxide solution and 500 mL of brine, dried (Na$_2$SO$_4$) and concentrated under reduced pressure to give a brown oil as residue. The oil was subjected to vacuum distillation to yield 134.9 g (70%) of yellow oil, bp 119° C.@ 0.2 mm.

Anal. Calculated for $C_8H_{14}ClNO_2$: C, 50.14; H, 7.36; N, 7.31. Found: C, 49.64; H, 7.43; N, 7.30.

PREPARATION 24

1-(4-Ethylaminophenyl)-4-phenylmethylpiperazine

N-[4-[4-(phenylmethyl)-1-piperazinyl]phenyl]acetamide is reduced with lithium aluminum hydride following standard chemical laboratory procedures to obtain the title compound.

PREPARATION 25

1-(4-Ethylaminophenyl)piperazine

A solution of 1-(4-ethylaminophenyl)-4-phenylmethylpiperazine in ethanol is catalytically hydrogenated at about 70° C. and 50 p.s.i., in the presence of 10% palladium on carbon. After hydrogen uptake ceases, the catalyst is removed by filtration and the filtrate concentrated to obtain the title compound.

EXAMPLE 1

3-Methyl-5-[4-(4-phenyl-1-piperazinyl)butyl]-2-oxazolidinone

To a refluxing solution of 13.6 g (0.071 mol) of 3-methyl-5-(4-chlorobutyl)-2-oxazolidinone and 11.5 g (0.071 mol) of phenylpiperazine in 60 mL of 2-butanol was added 21 g of potassium carbonate finely ground in 2-butanol. The addition of potassium carbonate was made in ca. 2 g portions at hour intervals. Reflux was continued for about 6 hours after the addition was complete. The mixture was filtered while hot and filtrate concentrated to an oil which solidified. The hydrochloric acid salt was prepared and the salt was recrystallized from absolute ethanol three times with the aid of activated charcoal to yield 2 g, mp 219°–224° (dec). The product was dissolved in water and the aqueous solution washed with ether, neutralized with dilute sodium hydroxide and filtered. The residue was dried and washed with ether, then recrystallized from isopropyl ether with the aid of activated charcoal (a little methanol was added to aid solution). The yield of product was 0.7 g, mp 82.5°–84° C.

Anal. Calculated for $C_{18}H_{27}N_3O_2$: C, 68.11; H, 8.57; N, 13.24. Found: C, 67.71; H, 8.50; N, 13.29.

EXAMPLE 2

5-[2-[4-(4-fluorophenyl)-1-piperazinyl]ethyl]-3-methyl-2-oxazolidinone

A mixture of 4.5 g (0.025 mol) of 1-(4-fluorophenyl)-piperazine, 4.1 g (0.025 mol) of 5-(2-chloroethyl)-3-methyl-2-oxazolidinone, 8.0 g (0.075 mol) of anhydrous sodium carbonate and 0.4 g of potassium iodide in 150 mL of n-butanol was heated at reflux for 20 h. The mixture was concentrated under reduced pressure and the residue partitioned between water and benzene. The benzene layer was washed with water and brine, dried ($Na_2SO_4$) and concentrated under reduced pressure to obtain a solid which was recrystallized from 2-propanol isopropyl/ether to obtain 5.7 g (74%) of white solid, mp 82°–84° C.

Anal. Calculated for $C_{16}H_{22}FN_3O_2$: C, 62.52; H, 7.21; N, 13.67. Found: C, 62.61; H, 7.22; N, 13.71.

EXAMPLE 3

3-Methyl-5-[2-[4-(2-pyridinyl)-1-piperazinyl]ethyl]-2-oxazolidinone

This compound was prepared according to the procedure of Example 2. A mixture of 4.1 g (0.025 mol) of 1-(2-pyridinyl)piperazine, 4.1 g (0.025 mol) of 5-(2-chloroethyl)-3-methyl-2-oxazolidinone, 8.0 g (0.075 mol) of anhydrous sodium carbonate and 0.4 g of potassium iodide in 150 mL of 1-butanol gave 5.5 g (75%) of white solid, mp 107.5°–109° C. (2-propanol).

Anal. Calculated for $C_{15}H_{22}N_4O_2$: C, 62.05; H, 7.64; N, 19.30. Found: C, 62.05; H, 7.65; N, 19.28.

EXAMPLE 4

5-[2-[4-(4-Methoxyphenyl)-1-piperazinyl]ethyl]-3-methyl-2-oxazolidinone

This compound was prepared according to the procedure of Example 2. A mixture of 2.4 g (0.012 mol) of 1-(4-methoxyphenyl)piperazine, 2.0 g (0.012 mol) of 5-(2-chloroethyl)-3-methyl-2-oxazolidinone, 4.2 g (0.04 mol) of anhydrous sodium carbonate and 0.4 g of potassium iodide in 100 mL of 1-butanol gave 2.4 g (63%) of pink solid, mp 103°–104° C. (2-propanol).

Anal. Calculated for $C_{17}H_{25}N_3O_3$: C, 63.93; H, 7.89; N, 13.16. Found: C, 63.89; H, 7.91; N, 13.21.

EXAMPLE 5

5-[2-[4-(4-Chlorophenyl)-1-piperazinyl]ethyl]-3-methyl-2-oxazolidinone

This compound was prepared according to the procedure of Example 2. A mixture of 4.9 g (0.025 mol) of 1-(4-chlorophenyl)piperazine, 4.1 g (0.025 mol) of 5-(2-chloroethyl)-3-methyl-2-oxazolidinone, 8.0 g (0.075 mol) of anhydrous sodium carbonate and 0.4 g of potassium iodide in 150 mL of 1-butanol gave 5.9 g (73%) of white solid, mp 113°–114° C. (2-propanol).

Anal. Calculated for $C_{16}H_{22}ClN_3O_2$: C, 59.35; H, 6.85; N, 12.98. Found: C, 59.38; H, 6.80; N, 12.74.

EXAMPLE 6

5-[2-[4-(3,4-Dichlorophenyl)-1-piperazinyl]ethyl]-3-methyl-2-oxazolidinone

This compound was prepared according to the procedure of Example 2. A mixture of 4.6 g (0.02 mol) of 1-(3,4-dichlorophenyl)piperazine, 3.3 g (0.02 mol) of 5-(2-chloromethyl)-3-methyl-2-oxazolidinone, 6.4 g (0.06 mol) of anhydrous sodium carbonate and 0.3 g of potassium iodide in 100 mL of 1-butanol gave 5.5 g (76%) of white solid, mp 89°–91° C. (2-propanol).

Anal. Calculated for $C_{16}H_{21}Cl_2N_3O_2$: C, 53.64; H, 5.91; N, 11.73. Found: C, 53.71; H, 5.89; N, 11.68.

EXAMPLE 7

3-Methyl-5-[2-[4-(4-methylphenyl)-1-piperazinyl]ethyl]-2-oxazolidinone

This compound was prepared according to the procedure of Example 2. A mixture of 3.5 g (0.02 mol) of 1-(4-methylphenyl)piperazine, 3.3 g (0.02 mol) of 5-(2-chloroethyl)-3-methyl-2-oxazolidinone, 6.4 g (0.06 mol) of anhydrous sodium carbonate and 0.3 g of potassium iodide in 100 mL of 1-butanol gave 4.2 g (69%) of white solid, mp 96°–97° C. (2-propanol).

Anal. Calculated for $C_{17}H_{25}N_3O_2$: C, 67.30; H, 8.31; N, 13.85. Found: C, 67.29; H, 8.35; N, 13.88.

EXAMPLE 8

5-[2-[4-(4-Bromophenyl)-1-piperazinyl]ethyl]-3-methyl-2-oxazolidinone

This compound was prepared according to the procedure of Example 2. A mixture of 3.6 g (0.015 mol) of 1-(4-bromophenyl)piperazine, 2.5 g (0.015 mol) of 5-(2-chloroethyl)-3-methyl-2-oxazolidinone, 4.8 g (0.045 mol) of anhydrous sodium carbonate and 0.4 g of potassium iodide in 100 mL of 1-butanol heated at reflux for 22 h gave 4.2 g (76%) of white solid, mp 125°–127° C. (2-propanol).

Anal. Calculated for $C_{16}H_{22}BrN_3O_2$: C, 52.18; H, 6.02; N, 11.41. Found: C, 51.92; H, 6.07; N, 11.34.

EXAMPLE 9

5-[2-[4-(4-Acetylphenyl)-1-piperazinyl]ethyl]-3-methyl-2-oxazolidinone

This compound was prepared according to the procedure of Example 2. A mixture of 4.1 g (0.02 mol) of 4-(1-piperazino)acetophenone (94%, Aldrich), 3.3 g (0.02 mol) of 5-(2-chloroethyl)-3-methyl-2-oxazolidinone, 6.4 (0.06 mol) of anhydrous sodium carbonate and 0.4 g of potassium iodide in 100 mL of 1-butanol gave 5.3 g (80%) of yellow solid, mp 142°–145° C. (2-propanol).

Anal. Calculated for $C_{18}H_{25}N_3O_2$: C, 65.24; H, 7.60; N, 12.68. Found C, 65.42; H, 7.77; N, 12.46.

EXAMPLE 10

3-Methyl-5-[2-[4-(4-nitrophenyl)-1-piperazinyl]ethyl]-2-oxazolidinone

This compound was prepared according to the procedure of Example 2. A mixture of 4.1 g (0.02 mol) of 1-(4-nitrophenyl)piperazine, 3.3 g (0.02 mol) of 5-(2-chloroethyl)-3-methyl-2-oxazolidinone, 6.4 g (0.06 mol) of anhydrous sodium carbonate and 0.4 g of potassium iodide in 100 mL of 1-butanol gave 5.3 g (79%) of yellow solid, mp 155°–156° C. (acetonitrile).

Anal. Calculated for $C_{16}H_{22}N_4O_4$: C, 57.47; H, 6.63; N, 16.76. Found: C, 57.37; H, 6.68; N, 16.67.

EXAMPLE 11

3-Methyl-5-[2-[4-[3-(trifluoromethyl)phenyl]-1-piperazinyl]ethyl]-2-oxazolidinone monohydrochloride hemihydrate This compound was prepared according to the procedure of Example 2. A mixture of 4.6 g (0.02 mol) of N-(α,α,α-trifluoro-m-tolyl)piperazine (95%, Aldrich), 3.3 g (0.02 mol) of 5-(2-chloroethyl)-3-methyl-2-oxazolidinone, 6.4 g (0.06 mol) of anhydrous sodium carbonate and 0.4 g of potassium iodide in 100 mL of 1-butanol gave a gum as residue. This gum was dissolved in ethyl and converted to the hydrochloride salt. The solid salt was recrystallized from 2-propanol/absolute ethanol to yield 6.3 g (80%) of white solid, mp 220°–221° C. (dec).

Anal. Calculated for $C_{17}H_{23}ClF_3N_3O_2 \cdot 0.5\ H_2O$: C, 50.69; H, 6.00; N, 10.43. Found: C, 50.17; H, 5.95; N, 10.27.

Anal. Calculated for $C_{17}H_{23}ClF_3N_3O_2 \cdot 0.75\ H_2O$: C, 50.13; H, 6.06; N, 10.32.

EXAMPLE 12

5-[2-[4-(2-chlorophenyl)-1-piperazinyl]ethyl]-3-methyl-2-oxazolidinone

This compound was prepared according to the procedure of Example 2. A mixture of 5.5 g (0.028 mol) of 1-(2-chlorophenyl)piperazine (Aldrich), 4.6 g (0.028 mol) of 5-(2-chloroethyl)-3-methyl-2-oxazolidinone, 8.9 g (0.08 mol) of anhydrous sodium carbonate and 0.4 g of potassium iodide in 150 mL of 1-butanol gave 6.8 g (75%) of off-white solid, mp 79.5°–81.5° C. (2-propanol).

Anal. Calculated for $C_{16}H_{22}ClN_3O_2$: C, 59.35; H, 6.85; N, 12.98. Found: C, 59.47; H, 6.92; N, 13.02.

EXAMPLE 13

5-[2-[4-(3-Chlorophenyl)-1-piperazinyl]ethyl]-3-methyl-2-oxazolidinone hydrochloride hemihydrate (2:3:1)

This compound was prepared according to the procedure of Example 2. A mixture of 3.6 g (0.018 mol) of 1-(3-chlorophenyl)piperazine (Aldrich), 3.0 g (0.018 mol) of 5-(2-chloroethyl)-3-methyl-2-oxazolidinone, 5.7 g (0.05 mol) of anhydrous sodium carbonate and 0.4 g of potassium iodide in 100 mL of 1-butanol gave a gum as a residue. The gum was converted to the hydrochloric acid salt and the solid was recrystallized from absolute ethanol to yield 4.2 g (60%) of off-white solid, mp 226°–229° C. (dec.).

Anal. Calculated for $C_{16}H_{22}ClN_3O_2 \cdot 1.5\ HCl \cdot 0.5\ H_2O$: C, 49.59; H, 6.37; N, 10.84. Found: C, 49.98; H, 6.21; N, 10.80.

EXAMPLE 14

5-[2-[4-[4-Chloro-3-(trifluoromethyl)phenyl]-1-piperazinyl]ethyl]-3-methyl-2-oxazolidinone (E)-2-butenedioate This compound was prepared according to the procedure of Example 2. A mixture of 4.0 g (0.15 mol) of 1-(4-chloro-3-trifluoromethylphenyl)piperazine (Emka-Chemie), 2.5 g (0.015 mol) of 5-(2-chloroethyl)-3-methyl-2-oxazolidinone, 5.3 g (0.05 mol) of anhydrous sodium carbonate and 0.4 g of potassium iodide in 100 mL of 1-butanol gave a gum as residue. The gum was converted to the fumaric acid salt and the solid was recrystallized from 95% ethanol to yield 5.7 g (78%) of white solid, mp 198°–201° C. (dec.).

Anal. Calculated for $C_{21}H_{25}ClF_3N_3O_6$: C, 49.66; H, 4.96; N, 8.27. Found: C, 49.69; H, 4.97; N, 8.23.

EXAMPLE 15

3-Methyl-5-[2-[4-(3-methylphenyl)-1-piperazinyl]ethyl]-2-oxazolidinone

This compound was prepared according to the procedure of Example 2. A mixture of 3.5 g (0.02 mol) of 1-(3-methylphenyl)piperazine (Emka-Chemie), 3.3 g (0.02 mol) of 5-(2-chloroethyl)-3-methyl-2-oxazolidinone, 6.4 g (0.06 mol) of anhydrous sodium carbonate and 0.4 g potassium iodide in 100 mL of 1-butanol gave 3.9 g (65%) of white solid, mp 72°–74° C. (2-propanol).

Anal. Calculated for $C_{17}H_{25}N_3O_2$: C, 67.30; H, 8.31; N, 13.85. Found: C, 67.44; H, 8.38; N, 13.86.

EXAMPLE 16

5-[2-[4-(2-Fluorophenyl)-1-piperazinyl]ethyl]-3-methyl-2-oxazolidinone

This compound was prepared according to the procedure of Example 2. A mixture of 3.6 g (0.02 mol) of 1-(2-fluorophenyl)piperazine (Emka-Chemie), 3.3 g (0.02 mol) of 5-(2-chloroethyl)-3-methyl-2-oxazolidinone, 6.4 g (0.06 mol) of anhydrous sodium carbonate and 0.3 g of potassium iodide in 100 mL of 1-butanol gave 3.7 g (61%) of white solid, mp 80°–82° C.

Anal. Calculated for $C_{16}H_{22}FN_3O_2$: C, 62.52; H, 7.21; N, 13.67. Found: C, 62.69; H, 7.27; N, 13.72.

EXAMPLE 17

3-Methyl-5-[2-[4-[4-(trifluoromethyl)phenyl]-1-piperazinyl]ethyl]-2-oxazolidinone This compound was prepared according to the procedure of Example 2. A mixture of 3.5 g (0.015 mol) of 1-(4-trifluoromethylphenyl)piperazine (Emka-Chemie), 2.5 g (0.015 mol) of 5-(2-chloroethyl)-3-methyl-2-oxazolidinone, 5.3 g (0.05 mol) of anhydrous sodium carbonate and 0.4 g of potassium iodide in 100 mL of 1-butanol gave 3.7 g (69%) of white solid, mp 116°–117° C. (2-propanol).

Anal. Calculated for $C_{17}H_{22}F_3N_3O_2$: C, 57.14; H, 6.20; N, 11.76. Found: C, 56.74; H, 6.24; N, 11.55.

EXAMPLE 18

5-[2-[4-(3-Methoxyphenyl)-1-Piperazinyl]Ethyl]-3-Oxazolidinone (E)-2-butendioate (1:1)

This compound was prepared according to the procedure of Example 2. A mixture of 2.9 g (0.015 mol) of 1-(3-methoxyphenyl)piperazine (Emka-Chemie), 2.5 g (0.015 mol) of 5-(2-chloroethyl)-3-methyl-2-oxazolidinone, 5.3 g (0.05 mol) of anhydrous sodium carbonate and 0.4 g of potassium iodide in 100 mL of 1-butanol gave a gum as residue. The gum was converted to the fumaric acid salt and the solid was recrystallized from 2-propanol to yield 4.7 g (72%) of white solid, mp 138°–140° C.

Anal. Calculated for $C_{21}H_{29}N_3O_7$: C, 57.92; H, 6.71; N, 9.65. Found: C, 57.89; H, 6.78; N, 9.61.

EXAMPLE 19

5-[2-[4-(2-Methoxyphenyl)-1-Piperazinyl]Ethyl]-3-Methyl-2-Oxazolidinone

This compound was prepared according to the procedure of Example 2. A mixture of 2.9 g (0.015 mol) of 1-(2-methoxyphenyl)piperazine (95%, Aldrich), 2.5 g (0.015 mol) of 5-(2-chloroethyl)-3-methyl-2-oxazolidinone, 5.3 g (0.05 mol) of anhydrous sodium carbonate and 0.4 g of potassium iodide in 100 mL of 1-butanol gave 3.0 g (63%) of off-white solid, mp 107°–108.5° C. (2-propanol).

Anal. Calculated for $C_{17}H_{25}N_3O_3$: C, 63.93; H, 7.89; N, 13.16. Found: C, 63.98; H, 8.01; N, 13.17.

EXAMPLE 20

5-[2-[4-(3,4-Dimethoxyphenyl)-1-Piperazinyl]Ethyl]-3-Methyl-2-Oxazolidinone

This compound was prepared according to the procedure of Example 2. A mixture of 3.3 g (0.015 mol) of 1-(3,4-dimethoxyphenyl)piperazine, 2.5 g (0.015 mol) of 5-(2-chloroethyl)-3-methyl-2-oxazolidinone, 5.3 g (0.05 mol) of anhydrous sodium carbonate and 0.3 g of potassium iodide in 100 mL of 1-butanol gave 2.2 g (42%) of white solid, mp 90°–92° C. (2-propanol).

Anal. Calculated for $C_{18}H_{27}N_3O_4$: C, 61.87; H, 7.79; N, 12.03. Found: C, 61.90; H, 7.87; N, 12.06.

EXAMPLE 21

3-Methyl-5-[2-[4-(3,4,5-Trimethoxyphenyl)-1-Piperazinyl]Ethyl]-2-Oxazolidinone

This compound was prepared according to the procedure of Example 2. A mixture of 3.8 g (0.015 mol) of 1-(3,4,5-trimethoxyphenyl)piperazine, 2.5 g (0.015 mol) of 5-(2-chloroethyl)-3-methyl-2-oxazolidinone, 5.3 g (0.05 mol) of anhydrous sodium carbonate and 0.3 g of potassium iodide in 100 mL of 1-butanol gave 2.4 g (42%) of white solid, mp 86°–88° C. (2-propanol).

Anal. Calculated for $C_{19}H_{29}N_3O_5$: C, 60.14; H, 7.70; N, 11.07. Found: C, 59.87; H, 7.78; N, 11.03.

EXAMPLE 22

3-Methyl-5-[2-[4-(2-Methylphenyl)-1-Piperazinyl]Ethyl]-2-Oxazolidinone

This compound was prepared according to the procedure of Example 2. A mixture of 3.5 g (0.02 mol) of 1-(2-methylphenyl)piperazine (Emka-Chemie), 3.3 g (0.02 mol) of 5-(2-chloroethyl)-3-methyl-2-oxazolidinone, 6.4 g (0.06 mol) of anhydrous sodium carbonate and 0.4 g of potassium iodide in 100 mL of 1-butanol gave 3.5 g (50%) of white solid, mp 55°–57° C. (isopropyl ether/2-propanol).

Anal. Calculated for $C_{17}H_{25}N_3O_2$: C, 67.30; H, 8.31; N, 13.85. Found: C, 67.21; H, 8.50; N, 13.84.

EXAMPLE 23

5-[2-[4-(2,6-Dimethylphenyl)-1-Piperazinyl]Ethyl]-3-Methyl-2-Oxazolidinone

This compound was prepared according to the procedure of Example 2. A mixture of 3.8 g (0.02 mol) of 1-(2,6-dimethylphenyl)piperazine (Emka-Chemie), 3.3 g (0.02 mol) of 5-(2-chloroethyl)-3-methyl-2-oxazolidinone, 6.4 g (0.06 mol) of anhydrous sodium carbonate and 0.4 g of potassium iodide in 100 mL of 1-butanol gave 3.6 g (57%) of white solid, mp 107°–108° C. (isopropyl ether/2-propanol).

Anal. Calculated for $C_{18}H_{27}N_3O_2$: C, 68.11; H, 8.57; N, 13.24. Found: C, 68.23; H, 8.78; N, 13.29.

EXAMPLE 24

5-[2-[4-(3,4-Dimethylphenyl)-1-Piperazinyl]Ethyl]-3-Methyl-2-Oxazolidinone

This compound was prepared according to the procedure of Example 2. A mixture of 3.8 g (0.02 mol) of 1-(3,4-dimethylphenyl)piperazine (Emka-Chemie), 3.3 g (0.02 mol) of 5-(2-chloromethyl)-3-methyl-2-oxazolidinone, 6.4 g (0.06 mol) of anhydrous sodium carbonate and 0.4 g of potassium iodide in 100 mL of 1-butanol gave 5.0 g (79%) of white powder, mp 96°–97° C. (2-propanol/isopropyl ether).

Anal. Calculated for $C_{18}H_{27}N_3O_2$: C, 68.11; H, 8.57; N, 13.24. Found: C, 68.18; H, 8.67; N, 13.30.

EXAMPLE 25

5-[2-[4-(3,5-Dichlorophenyl)-1-Piperazinyl]Ethyl]-3-Methyl-2-Oxazolidinone

This compound was prepared according to the procedure of Example 2. A mixture of 4.6 g (0.02 mol) of 1-(3,5-dichlorophenyl)piperazine (Emka-Chemie), 3.3 g (0.02 mol) of 5-(2-chloromethyl)-3-methyl-2-oxazolidinone, 6.4 g (0.06 mol) of anhydrous sodium carbonate and 0.4 g of potassium iodide in 100 mL of 1-butanol gave 5.4 g (75%) of white solid, mp 89°–90° C. (2-propanol/isopropyl ether).

Anal. Calculated for $C_{16}H_{21}N_3O_2$: C, 53.64; H, 5.91; N, 11.73. Found: C, 53.61; H, 6.02; N, 11.72.

EXAMPLE 26

5-[2-[4-(3,5-Dimethoxyphenyl)-1-Piperazinyl]Ethyl]-3-Methyl-2-Oxazolidinone

This compound was prepared according to the procedure of Example 2. A mixture of 3.3 g (0.015 mol) of 1-(3,5-dimethoxyphenyl)piperazine (Emka-Chemie), 2.5 g (0.015 mol) of 5-(2-chloromethyl)-3-methyl-2-oxazolidinone, 5.4 g (0.05 mol) of anhydrous sodium carbonate and 0.4 g of potassium iodide in 100 mL of 1-butanol gave 3.9 g (73%) of off-white solid, mp 85°–87° C. (2-propanol).

Anal. Calculated for $C_{18}H_{27}N_3O_4$: C, 61.87; H, 7.79; N, 12.03. Found: C, 61.79; H, 7.82; N, 12.01.

EXAMPLE 27

S-(−)-3-Methyl-5-[2-(4-Phenyl-1-Piperazinyl)Ethyl]-2-Oxazolidinone

This compound was prepared according to the procedure of Example 2. A mixture of 8.1 g (0.05 mol) of 1-phenylpiperazine, 8.2 g (0.05 mol) of S-(−)-5-(2-chloroethyl)-3-methyl-2-oxazolidinone, 15.9 g (0.15 mol) of anhydrous sodium carbonate and 0.6 g of potassium iodide in 200 mL of 1-butanol gave 13.0 g (90%) of white solid, mp 119°-123° C. (2-propanol); $[\alpha]_D^{25} = -35.50°$ (methanol).

Anal. Calculated for $C_{16}H_{23}N_3O_2$: C, 66.41; H, 8.01; N, 14.52. Found: C, 66.52; H, 8.14; N, 14.55.

A portion of this solid was converted to the maleic acid salt to give a white solid, mp 137°-138° C. (absolute ethanol); $[\alpha]_D^{25} = -21.3°$ (methanol).

Anal. Calculated for $C_{20}H_{27}N_3O_6$: C, 59.25; H, 6.71; N, 10.36. Found: C, 59.30; H, 6.77; N, 10.38.

EXAMPLE 28

R-(+)-3-Methyl-5-[2-(4-Phenyl-1-Piperazinyl)Ethyl]-2-Oxazolidinone

This compound was prepared according to the procedure of Example 2. A mixture of 8.1 g (0.05 mol) of 1-phenylpiperazine, 8.2 g (0.05 mol) of R-(+)-2-(chloroethyl)-3-methyl-2-oxazolidinone, 15.9 g (0.15 mol) of anhydrous sodium carbonate and 0.6 g of potassium iodide in 200 mL of 1-butanol gave 11.9 g (82%) of white solid, mp 122°-125° C. (2-propanol); $[\alpha]_D^{25} = +37.5°$ (methanol).

Anal. Calculated for $C_{16}H_{23}N_3O_2$: C, 66.41; H, 8.01; N, 14.52. Found: C, 66.53; H, 8.17; N, 14.54.

A portion of this solid was converted to the maleic acid salt to give a white solid, mp 140°-142° C. (absolute ethanol); (methanol); $[\alpha]_D^{25} = +27.0°$ (methanol).

Anal. Calculated for $C_{20}H_{27}N_3O_6$: C, 59.25; H, 6.71; N, 10.36. Found: C, 59.33; H, 6.82; N, 10.42.

EXAMPLE 29

5-[2-[4-(3-Ethylphenyl)-1-Piperazinyl]Ethyl]-3-Methyl-2-Oxazolidinone Dihydrochloride A mixture of 12.2 g (0.064 mol) of 1-(3-ethylphenyl)-piperazine, 12.6 g (0.077 mol) of 5-(2-chloroethyl)-3-methyl-2-oxazolidinone, 27.1 g (0.255 mol) of anhydrous sodium carbonate, and 0.5 g (0.003 mol) of potassium iodide in 300 mL of 1-butanol was heated at reflux for 16 h. The mixture was concentrated under reduced pressure and the residue partitioned between 300 mL of benzene and 300 mL of water. The benzene layer was washed with water and brine, dried (MgSO$_4$) and concentrated under reduced pressure to yield 21.0 g (100%) of a gold-colored, viscous oil.

A 6.0 g portion of the oil was converted to the dihydrochloric acid salt and the solid was recrystallized from methanol to yield 4.6 g (62%) of white solid, mp 200°-203° C.

Anal. Calculated for $C_{18}H_{29}Cl_2N_3O_2$: C, 55.39; H, 7.49; N, 10.77. Found: C, 55.20; H, 7.61; N, 10.74.

EXAMPLE 30

5-[2-[4-(4-Fluoro-3-Methylphenyl)-1-Piperazinyl]Ethyl]-3-Methyl-2-Oxazolidinone Ethanedioate (1:1)

A mixture of 5.5 g (0.029 mol) of 1-(4-fluoro-3-methylphenyl)piperazine, 5.6 g (0.034 mol) of 5-(2-chloroethyl)-3-methyl-2-oxazolidinone, 12.1 g (0.114 mol) of anhydrous sodium carbonate, and 0.3 g (0.002 mol) of potassium iodide in 250 mL of 1-butanol was heated at reflux for 16 h. The mixture was concentrated under reduced pressure and the residue partitioned between 300 mL of benzene and 300 mL of water. The benzene layer was washed with water and brine, dried (MgSO$_4$) and concentrated under reduced pressure to give a light-pink oil. The oil was converted to the oxalic acid salt and the solid was recrystallized from methanol to yield 10.0 g (81%) of white solid, mp 200°-203° C.

Anal. Calculated for $C_{19}H_{26}FN_3O_6$: C, 55.47; H, 6.37; N, 10.21. Found: C, 55.38; H, 6.47; N, 10.16.

EXAMPLE 31

5-[2-[4-(3-Fluorophenyl)-1-Piperazinyl]Ethyl]-3-Methyl-2-Oxazolidinone

A mixture of 8.0 g (0.044 mol) of 1-(3-fluorophenyl)-piperazine, 8.0 g (0.049 mol) of 5-(2-chloroethyl)-3-methyl-2-oxazolidinone, 18.7 g (0.176 mol) of anhydrous sodium carbonate, and 0.3 g (0.002 mol) of potassium iodide in 250 mL of 1-butanol was heated at reflux for 16 h. The mixture was concentrated under reduced pressure and the residue partitioned between 300 mL of benzene and 300 mL of water. The benzene layer was washed with water and brine, dried (MgSO$_4$) and concentrated under reduced pressure to give a light-yellow solid. The solid was recrystallized from benzene-petroleum ether (30°-60° C.) to yield 9.5 g (70%) of white soldi, mp 92°-93° C.

Anal. Calculated for $C_{16}H_{22}FN_3O_2$: C, 62.52; H, 7.21; N, 13.67. Found: C, 62.47; H, 7.28; N, 13.65.

EXAMPLE 32

3-Methyl-5-[3-(4-Phenyl-1-Piperazinyl)Propyl]-2-Oxazolidinone Dihydrochloride Hemihydrate This compound was prepared according to the procedure of Example 2. A mixture of 3.2 g (0.02 mol) of 1-phenylpiperazine, 3.6 g (0.02 mol) of 5-(3-chloropropyl)-3-methyl-2-oxazolidinone, 8.0 g (0.075 mol) of anhydrous sodium carbonate, and 0.4 g of potassium iodide in 100 mL of 1-butanol gave a gum as residue. The gum was converted to the hydrochloric acid salt and the solid was recrystallized from absolute ethanol containing a few drops of water to yield 4.8 g (63%) of white solid, mp 180°-191° C. (dec).

Anal. Calculated for $C_{17}H_{27}Cl_2N_3O_2$108 0.5 H$_2$O: C, 52.99; H, 7.32; N, 10.90. Found: C, 53.77; H, 7.48; N, 11.07.

Anal. Calculated for $C_{17}H_{27}Cl_2N_3O_2 \bullet 0.25$ H$_2$O: C, 53.62; H, 7.28; N, 11.03.

EXAMPLE 33

3-Methyl-5-(4-Phenyl-1-Piperazinylmethyl)-2-Oxazolidinone

This compound was prepared according to the procedure of Example 2. A mixture of 3.2 g (0.02 mol) of 1-phenylpiperazine, 3.0 g (0.02 mol) of 5-(chloromethyl)-3-methyl-2-oxazolidinone, 8.0 g (0.075 mol) of anhydrous sodium carbonate, and 0.4 g of potassium iodide in 100 mL of 1-butanol gave a brown oil as residue. The oil was converted to the dioxalate and the solid was recrystallized from acetonitrile-dimethylformamide but did not give a correct combustion analysis. The salt was partitioned between methylene chloride and a 4% sodium hydroxide solution. The organic layer was dried (Na$_2$SO$_4$) and concentrated to yield 0.9 g (16%) of white solid, mp 110°-112° C. (2-propanol).

Anal. Calculated for $C_{15}H_{21}N_3O_2$: C, 65.43; H, 7.69; N, 15.26. Found: C, 65.46; H, 7.78; N, 15.21.

EXAMPLE 34

3-(1-Methylethyl)-5-[2-(4-Phenyl-1-Piperazinyl)Ethyl]-2-Oxazolidinone

This compound was prepared according to the procedure of Example 2. A mixture of 3.2 g (0.02 mol) of 1-phenylpiperazine, 3.8 g (0.02 mol) of 5-(2-chloromethyl)-3-(1-methylethyl)-2-oxazolidinone, 8.0 g (0.075 mol) of anhydrous sodium carbonate, and 0.4 g of potassium iodide in 100 mL of 1-butanol gave 4.1 g (65%) of white solid, mp 74°–75° C. (2-propanol/isopropyl ether).

Anal. Calculated for $C_{18}H_{27}N_3O_2$: C, 68.11; H, 8.57; N, 13.24. Found: C, 68.06; H, 8.65; N, 13.23.

EXAMPLE 35

5-[2-[4-(2-Chlorophenyl)-1-Piperazinyl]Ethyl]-2-Oxazolidinone Maleate

A stirred mixture of 8.3 g (0.056 mol) of 5-(2-chloroethyl)-2-oxazolidinone, 11 g (0.056 mol) of 1-(2-chlorophenyl)piperazine and 7.7 g (0.056 mol) of potassium carbonate in 150 ml of 2-propanol was heated at reflux temperature for 18 h. The mixture was filtered and the filtrate concentrated at reduced pressure. The residue was dissolved in 2-propanol and treated with a solution of 6.9 g (0.0595 mol) of maleic acid in warm methanol. The resulting maleic acid salt was collected and recrystallized several times from a 2-butanone/methanol mixture to obtain 5.8 g (25%) of solid, mp 166°–168.5° C.

Anal. Calculated for $C_{29}H_{24}ClN_3O_6$: C, 53.58; H, 5.68; N, 9.87. Found: C, 53.56; H, 5.94; N, 9.97.

EXAMPLE 36

5-[2-[4-(4-Chlorophenyl)-1-Piperazinyl]Ethyl]-2-Oxazolidinone Difumerate

The title compound was prepared from 5-(2-chloroethyl)-2-oxazolidinone and 1-(4-chlorophenyl)piperazine following the procedure of Example 35. The difumaric acid salt was prepared, mp 202°–206.5° C.

EXAMPLE 37

5-[(4-Phenyl-1-Piperazinyl)Methyl]-2-Oxazolidinone Maleate

Following the procedure of Example 35, the free base was prepared from 5-chloromethyl-2-oxazolidinone and 1-phenylpiperazine. The product was converted to the maleic acid salt, mp 166°–168° C.

EXAMPLE 38

5-[4-(3-Trifluoromethylphenyl)-1-Piperazinyl]Methyl-2-Oxazolidinone

Following the procedure of Example 35, the title compound was prepared from 5-chloromethyl-2-oxazolidinone and 1-(3-trifluoromethylphenyl)piperazine, mp 122°–124° C.

EXAMPLE 39

5-[2-[4-(2-Fluorophenyl)Piperazinyl]Ethyl]-2-Oxazolidinone

Following the procedure of Example 35, the title compound was prepared from 5-(2-chloroethyl)-2-oxazolidinone and 1-(2-fluorophenyl)piperazine, mp 121°–124° C.

EXAMPLE 40

5-[2-[4-(3-Chlorophenyl)-1-Piperazinyl]Ethyl]-2-Oxazolidinone Maleate

Following the procedure of Example 35, the title compound is prepared from 5-(2-chloroethyl)-2-oxazolidinone and 1-(3-chlorophenyl)piperazine in 38% yield, mp 121°–124° C.

EXAMPLE 41

The following Formula I compounds were disclosed in U.S. Pat. No. 3,419,559.
a. 3-benzyl-5-[2-(4-phenyl-1-piperazinyl)ethyl]-2-oxazolidinone.
b. 5-[2-(4-phenyl-1-piperazinyl)ethyl]-2-oxazolidinone.
c. 3-cyclohexyl-5-[2-(4-phenyl-1-piperazinyl)ethyl]-2-oxazolidinone.
d. 3-methyl-5-[2-(4-phenyl-1-piperazinyl)ethyl]-2-oxazolidinone.
e. 1-ethyl-5-[2-(4-phenyl-1-piperazinyl)ethyl]-2-oxazolidinone.
f. 5-[2-[4-(2-methylphenyl)-1-piperazinyl]ethyl]-2-oxazolidinone.
g. 5-[2-[4-(4-methylphenyl)-1-piperazinyl]ethyl]-2-oxazolidinone.
h. 5-[2-[4-(2-methoxyphenyl)-1-piperazinyl]ethyl]-2-oxazolidinone.
i. 5-[2-[4-(4-fluorophenyl)-1-piperazinyl]ethyl]-2-oxazolidinone.
j. 5-[2-[4-(2-pyridinyl)-1-piperazinyl]ethyl]-2-oxazolidinone.
k. 5-[2-[4-(2-chlorophenyl)-1-piperazinyl]ethyl]-2-oxazolidinone.
l. 5-[2-[4-(3-trifluoromethylphenyl)-1-piperazinyl]ethyl]-2-oxazolidinone.

EXAMPLE 42

5-[2-[4-(4-Aminophenyl)-1-piperidinyl]ethyl]-3-methyl-2-oxazolidinone

A solution of 3-methyl-5-[2-[4-(4-nitrophenyl)-1-piperazinyl]ethyl]-2-oxazolidinone in 95% ethanol is subjected to catalytic hydrogenation in the presence of 10% palladium on carbon catalyst at room temperature on a Parr apparatus. The catalyst is removed by filtration and the filtrate concentrated to obtain the title compound.

EXAMPLE 43

5-[2-[4-(4-Dimethylaminophenyl)-1-piperazinyl]ethyl]-3-methyl-2-oxazolidinone

A mixture of 5-[2-[4-(4-aminophenyl)-1-piperazinyl]ethyl]-3-methyl-2-oxazolidinone (0.015 mol), 88% formic acid (10 mL) and 37% formalin (20 mL) is heated at reflux temperature for 15 h, cooled, and diluted with water. The mixture is basified to pH 8 and the product isolated using standard laboratory techniques.

EXAMPLE 44

5-[2-[4-(4-N-acetylaminophenyl)-1-piperazinyl]ethyl]-3-methyl-2-oxazolidinone

Following the procedure of Example 2, the title compound is prepared from N-[4-(1-piperazinyl)phenyl]acetamide and 5-(2-chloroethyl)-3-methyl-2-oxazolidinone.

EXAMPLE 45

5-[2-[4-(4-cyanophenyl)-1-piperazinyl]ethyl]-3-methyl-2-oxazolidinone

Following the procedure of Example 2, the title compound is prepared from 4-(1-piperazinyl)benzonitrile and 5-(2-chloromethyl)-3-methyl-2-oxazolidinone.

EXAMPLE 46

4-[4-[2-(3-methyl-2-oxazolidinon-5-yl)ethyl]-1-piperazinyl]benzamide

Following the procedure of Example 2, the title compound is prepared from 5-(2-chloroethyl)-3-methyl-2-oxazolidinone and 4-(1-piperazinyl)benzamide.

EXAMPLE 47

4-[4-[2-(3-methyl-2-oxazolidinon-5-yl)ethyl]-1-piperazinyl]benzoic acid ethyl ester Following the procedure of Example 2, the title compound is prepared from 5-(2-chloroethyl)-3-methyl-2-oxazolidinone and 4-(1-piperazinyl)benzoic acid ethyl ester.

EXAMPLE 48

5-[2-[4-(4-ethylaminophenyl)-1-piperazinyl]ethyl]-3-methyl-2-oxazolidinone

Following the procedure of Example 2, the title compound is prepared from 5-(2-chloroethyl)-3-methyl-2-oxazolidinone and 1-(4-ethylaminophenyl)piperazine.

EXAMPLE 49

5-[2-(4-phenyl-1-piperazinyl)ethyl]-3-phenyl-2-oxazolidinone

Following the procedure of Example 2, the title compound was prepared from 5-(2-chloroethyl)-3-phenyl-2-oxazolidinone and 1-phenylpiperazine.

EXAMPLE 50

3-(3-Chlorophenyl)-5-[2-(4-phenyl-1-piperazinyl)ethyl]-2-oxazolidinone

Following the procedure of Example 2, the title compound is prepared from 5-(2-chloroethyl)-3-(3-chlorophenyl)-2-oxazolidinone and 1-phenylpiperazine.

TABLE

Formula I Compounds

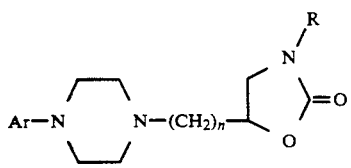

| Example | Ar | n | R |
|---|---|---|---|
| 1 | $C_6H_5-$ | 4 | $CH_3$ |
| 2 | $4-FC_6H_4-$ | 2 | $CH_3$ |
| 3 | 2-pyridinyl | 2 | $CH_3$ |
| 4 | $4-CH_3OC_6H_4-$ | 2 | $CH_3$ |
| 5 | $4-ClC_6H_4-$ | 2 | $CH_3$ |
| 6 | $3,4-diClC_6H_3-$ | 2 | $CH_3$ |
| 7 | $4-CH_3C_6H_4-$ | 2 | $CH_3$ |
| 8 | $4-BrC_6H_4$ | 2 | $CH_3$ |
| 9 | $4-CH_3\overset{O}{\underset{\|\|}{C}}C_6H_4-$ | 2 | $CH_3$ |
| 10 | $4-NO_2C_6H_4-$ | 2 | $CH_3$ |
| 11 | $3-CF_3C_6H_4-$ | 2 | $CH_3$ |
| 12 | $2-ClC_6H_4-$ | 2 | $CH_3$ |
| 13 | $3-ClC_6H_4-$ | 2 | $CH_3$ |
| 14 | $4-Cl-3-CF_3-C_6H_3-$ | 2 | $CH_3$ |
| 15 | $3-CH_3C_6H_4-$ | 2 | $CH_3$ |
| 16 | $2-FC_6H_4-$ | 2 | $CH_3$ |
| 17 | $4-CF_3C_6H_4-$ | 2 | $CH_3$ |
| 18 | $3-CH_3OC_6H_4-$ | 2 | $CH_3$ |
| 19 | $2-CH_3OC_6H_4-$ | 2 | $CH_3$ |

TABLE-continued

Formula I Compounds

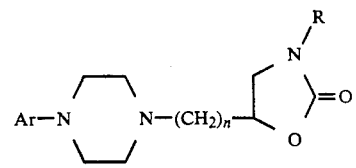

| Example | Ar | n | R |
|---|---|---|---|
| 20 | $3,4-diCH_3OC_6H_3-$ | 2 | $CH_3$ |
| 21 | $3,4,5-triCH_3OC_6H_2$ | 2 | $CH_3$ |
| 22 | $2-CH_3C_6H_4-$ | 2 | $CH_3$ |
| 23 | $2,6-diCH_3C_6H_3-$ | 2 | $CH_3$ |
| 24 | $3,4-diCH_3C_6H_3-$ | 2 | $CH_3$ |
| 25 | $3,5-diClC_6H_3-$ | 2 | $CH_3$ |
| 26 | $3,5-diMeOC_6H_3-$ | 2 | $CH_3$ |
| 27 | $C_6H_5-$ | 2 | $CH_3$ (S-(−)isomer) |
| 28 | $C_6H_5-$ | 2 | $CH_3$ (R-(+)isomer) |
| 29 | $3-C_2H_5C_6H_4-$ | 2 | $CH_3$ |
| 30 | $4-F-3-CH_3C_6H_3-$ | 2 | $CH_3$ |
| 31 | $3-F-C_6H_4-$ | 2 | $CH_3$ |
| 32 | $C_6H_5-$ | 3 | $CH_3$ |
| 33 | $C_6H_5-$ | 1 | $CH_3$ |
| 34 | $C_6H_5-$ | 2 | $CH(CH_3)_2$ |
| 35 | $2-ClC_6H_4-$ | 2 | H |
| 36 | $4-ClC_6H_4-$ | 2 | H |
| 37 | $C_6H_5-$ | 1 | H |
| 38 | $3-CF_3C_6H_4-$ | 1 | H |
| 39 | $2-FC_6H_4-$ | 2 | H |
| 40 | $3-ClC_6H_4-$ | 2 | H |
| 41a | $C_6H_5-$ | 2 | benzyl |
| 41b | $C_6H_5-$ | 2 | H |
| 41c | $C_6H_5-$ | 2 | cyclohexyl |
| 41d | $C_6H_5-$ | 2 | methyl |
| 41e | $C_6H_5-$ | 2 | ethyl |
| 41f | $2-CH_3C_6H_4-$ | 2 | H |
| 41g | $4-CH_3C_6H_4-$ | 2 | H |
| 41h | $2-CH_3OC_6H_4-$ | 2 | H |
| 41i | $4-FC_6H_4-$ | 2 | H |
| 41j | 2-pyridinyl | 2 | H |
| 41k | $2-ClC_6H_4-$ | 2 | H |
| 41l | $3-CF_3C_6H_4-$ | 2 | H |
| 42 | $4-NH_2C_6H_4-$ | 2 | $CH_3$ |
| 43 | $4-(CH_3)_2NC_6H_4-$ | 2 | $CH_3$ |
| 44 | $4-CH_3C(O)NHC_6H_4-$ | 2 | $CH_3$ |
| 45 | $4-CNC_6H_4-$ | 2 | $CH_3$ |
| 46 | $4-NH_2C(O)C_6H_4-$ | 2 | $CH_3$ |
| 47 | $4-C_2H_5OC(O)C_6H_4-$ | 2 | $CH_3$ |
| 48 | $4-C_2H_5NHC_6H_4-$ | 2 | $CH_3$ |
| 49 | $C_6H_5-$ | 2 | $C_6H_5$ |
| 50 | $C_6H_5-$ | 2 | $3-ClC_6H_4$ |

PHARMACOLOGY METHODS

Antiallergy Screening Method—Rats

As stated above, the primary screening method used to demonstrate antiallergy properties of the compounds of Formula I is a modification of the procedure of R. R. Martel and J. Klicius, International Archives Allergy Appl. Immunology, Vol. 54, pp 205-2-0 (1977) which measures the effect of oral administration of the compounds on the volume of a rat paw which was previously injected with anti-egg albumin serum following egg albumin challenge. The procedure is as follows: Fed rats are injected in the right hind paw with 0.2 ml of rat anti-egg albumin serum at a dilution previously shown to produce significant edema upon antigen challenge. The animals are then fasted, but allowed water ad libitum. The next day the rats are randomized into groups of 6 by means of tables generated by the IBM scambler. Random number tables are used to determine the groups receiving the control, reference and test articles. On the test day, the right foot volume of each rat is determined plethysmographically using the hairline as the reference point. Volume of this foot is measured with a mercury filled tube that is connected to a P23A Statham[R] pressure transducer that in turn is connected to a linear Cole Parmer[R] recorder (Model No. 225). The instrument is adjusted so that a pen deflection of 50 mm is equivalent to 1 ml volume. Separately, the reference and test compounds and control articles are dissolved or suspended in 0.5% Tween 80 in distilled water. Sonification is used to facilitate dissolution or reduce particle size. The animals are dosed orally (10 mg/kg) at 1 hr prior to the intravenous injection of the antigen, 2 mg of egg albumin in 0.2 ml of sterile saline. Thirty minutes later the right foot volume is measured again and edema is determined by difference. Results are expressed as the average foot edema (ml) ±S.D. A significant decrease ($p<0.05$) in edema of the treated group from that of the control group is considered as indicative of antiallergic activity. The results are acceptable only if the group receiving the reference article (aminophylline) shows a significant decrease in foot edema. The foot volume for each animal is measured twice, once prior to dosing and again 30 min following the intravenous administration of antigen. Data is analyzed with the Dunnett's t-test that compares several treated groups with a control group. Differences between groups are determined by the studentized Range Test. Regression analysis may be used to determine relative potency. A majority of the example compounds tested caused a reduction in paw volume from 50% to 91% as compared with the pre-antigen challenge volume. One compound (example 20) caused an increase in paw volume (11%). Data for representative compounds are shown in Table II.

TABLE II

Antiallergy Screening Test. Passive Foot Anaphylaxis

| Example No. | % Reduction in Paw Volume | |
| --- | --- | --- |
| | Test[1] | Reference[2] |
| 1 | −91 | −55 |
| 4 | −24 | −70 |
| 5 | −82 | −70 |
| 9 | −32 | −60 |
| 12 | −17 | −73 |
| 15 | −80 | −68 |
| 17 | −8 | −68 |
| 22 | −48 | −52 |
| 23 | −2 | −52 |
| 27 | −68 | −77 |
| 30 | −60 | −55 |
| 32 | −87 | −69 |
| 41c | −71 | −55 |

[1]test drug 10 mg/kg/PO
[2]aminophylline 100 mg/PO

Pharmaceutical Compositions and Administration

Compositions for administration to living animals are comprised of at least one of the compounds of Formula I according to the antiallergy method of the invention in association with a pharmaceutical carrier or excipient. Effective quantities of the compounds may be administered in any one of various ways, for example, orally as in elixirs, capsules, tablets or coated tablets, parenterally in the form of sterile solutions, suspensions, and in some cases intravenously in the form of sterile solutions, intranasally and to the throat or bronchial region in the form of drops, sprays, aerosols and powders, etc. or cutaneously as topical ointments, solutions, powders, etc. Suitable tableting excipients include lactose, potato and maize starches, talc, gelatin, stearic and silica acids, magnesium stearate and polyvinyl pyrrolidone.

For parenteral administration, the carrier or excipient can be composed of a sterile parenterally acceptable liquid; e.g., water or arachis oil contained in ampoules.

Advantageously, the compositions are formulated as dosage units, each unit being adapted to supply a fixed dose of active ingredients. Tablets, coated tablets, capsules, ampoules, sprays and suppositories are examples of preferred dosage forms. It is only necessary that the active ingredient constitute an effective amount such that a suitable effective dosage will be consistent with the dosage form employed, in multiples if necessary. The exact individual dosages, as well as daily dosage, will of course be determined according to standard medical principles under the direction of a physician suitable effective dosage will be consistent with the dosage form employed, in multiples if necessary. The exact individual dosages, as well as daily dosage, will of course be determined according to standard medical principles under the direction of a physician or veterinarian. Generally, the pharmacology tests on guinea pigs in comparison to certain other anti-allergy drugs suggest an effective dose for an adult will be in the range of 0.5 to 10 mg for the more active compounds with a daily dosage amounting to about 2 to 40 mg/day.

Based on the animal data, unit dosages containing an amount of compound equivalent to about 0.01 to 0.1 mg of active drug per kilogram of body weight are contemplated. Daily dosages to about 0.05 to 0.5 mg/kg of body weight are contemplated for humans and obviously several small dosage forms may be administered at one time. However, the amount of the active compounds administered need not be limited by these contemplations due to uncertainty in transposing animal data to human treatment.

Various modifications and equivalents will be apparent to one skilled in the art and may be made in the compounds, methods of treatment and compositions of the present invention without departing from the spirit or scope thereof, and it is therefore to be understood that the invention is to be limited only by the scope of the appended claims.

What is claimed is:

1. A method of treating allergies in warm-blooded animals by administering thereto a therapeutically effective amount of an antiallergy compound having the formula

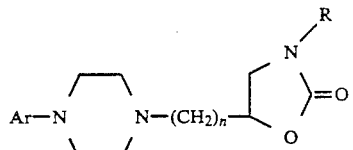

where R is hydrogen, loweralkyl, phenyl, substituted phenyl, phenylloweralkyl, or cycloalkyl; n is 1–4, and Ar is pyridinyl, phenyl or phenyl substituted by 1 to 3 substituents selected from halogen, loweralkyl, loweralkoxy, trifluoromethyl, nitro, acetyl, amino, loweralkylamino, diloweralkylamino, acetylamino, cyano, aminocarbonyl, or carboxylate, the stereoisomers, and pharmaceutically acceptable salts thereof.

2. A method according to claim 1 where the compound used is 3-benzyl-5-[2-(4-phenyl-1-piperazinyl)e- thyl]-2-oxazolidinones, a stereoisomer, or a pharmaceutically acceptable salt thereof.

3. A method according to claim 1 where the compound used is 3-cyclohexyl-5-[2-(4-phenyl-1-piperazinyl)ethyl]-2-oxazolidinone, a stereoisomer, or a pharmaceutically acceptable salt thereof.

4. The method according to claim 1 where the compound used is 1-ethyl-5-[2-(4-phenyl-1-piperazinyl)ethyl]-2-oxazolidinone, a stereoisomer, or a pharmaceutically acceptable salt thereof.

5. The method according to claim 1 where the compound used is 3-methyl-5-[4-(4-phenyl-1-piperazinyl)butyl]-2-oxazolidinone, a stereoisomer, or a pharmaceutically acceptable salt thereof.

6. The method according to claim 1 where the compoud used is 5-[2-[4-(4-fluorophenyl)-1-piperazinyl]ethyl]-3-methyl-2-oxazolidinone, a stereoisomer, or a pharmaceutically acceptable salt thereof.

7. The method according to claim 1 where the compound used is 5-[2-[4-(4-chlorophenyl)-1-piperazinyl]ethyl]-3-methyl-2-oxazolidinone, a stereoisomer, or a pharmaceutically acceptable salt thereof.

8. The method according to claim 1 where the compound used is 3-methyl-5-[2-[4-(3-methylphenyl)-1-piperazinyl]ethyl]-2-oxazolidinone, a stereoisomer, or a pharmaceutically acceptable salt thereof.

9. The method according to claim 1 where the compound used is S-(−)-3-methyl-5-[2-(4-phenyl)-1-piperazinyl)ethyl]-2-oxazolidinone, or a pharmaceutically acceptable salt thereof.

10. The method according to claim 1 where the compound used is R-(+)-3-methyl-5-[2-(4-phenyl)-1-piperazinyl)ethyl]-2-oxazolidinone or a pharmaceutically acceptable salt thereof.

11. The method according to claim 1 where the compound used is 5-[2-[4-(3-ethylphenyl)-1-piperazinyl]ethyl]-3-methyl-2-oxazolininone or a pharmaceutically acceptable salt thereof.

12. The method according to claim 1 where the compound used is 3-methyl-5-[3-(4-phenyl-1-piperazinyl)propyl]-2-oxazolidinone or a pharmaceutically acceptable salt thereof.

* * * * *